(12) United States Patent
Amari et al.

(10) Patent No.: US 11,571,371 B2
(45) Date of Patent: *Feb. 7, 2023

(54) METHOD FOR MANUFACTURING COATING FILM BY ELECTROSTATIC SPRAYING

(71) Applicant: Kao Corporation, Tokyo (JP)

(72) Inventors: Naomi Amari, Ichikai-machi (JP); Takehiko Tojo, Utsunomiya (JP); Kenta Mukai, Utsunomiya (JP)

(73) Assignee: Kao Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/474,435

(22) PCT Filed: Dec. 27, 2017

(86) PCT No.: PCT/JP2017/047079
§ 371 (c)(1),
(2) Date: Jun. 27, 2019

(87) PCT Pub. No.: WO2018/124227
PCT Pub. Date: Jul. 5, 2018

(65) Prior Publication Data
US 2019/0343731 A1 Nov. 14, 2019

(30) Foreign Application Priority Data
Dec. 28, 2016 (JP) .............................. JP2016-255100

(51) Int. Cl.
*A61K 8/34* (2006.01)
*A61Q 1/02* (2006.01)
*A61K 8/02* (2006.01)
*A61K 8/31* (2006.01)
*A61K 8/35* (2006.01)
*A61M 35/00* (2006.01)
*A61Q 19/00* (2006.01)

(52) U.S. Cl.
CPC .............. *A61K 8/022* (2013.01); *A61K 8/027* (2013.01); *A61K 8/31* (2013.01); *A61K 8/345* (2013.01); *A61K 8/35* (2013.01); *A61M 35/003* (2013.01); *A61Q 19/00* (2013.01); *A61K 2800/262* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 5,945,111 A | 8/1999 | Esser | |
| 6,252,129 B1* | 6/2001 | Coffee | A61F 13/00085 239/3 |
| 6,461,626 B1 | 10/2002 | Rabe et al. | |
| 6,514,504 B1 | 2/2003 | Yen et al. | |
| 6,531,142 B1 | 3/2003 | Rabe et al. | |
| 7,823,809 B2* | 11/2010 | Yamaguchi | B05B 5/0533 239/690.1 |
| 2002/0187181 A1 | 12/2002 | Godbey et al. | |
| 2002/0192252 A1 | 12/2002 | Ying Yen et al. | |
| 2003/0203991 A1 | 10/2003 | Schottman et al. | |
| 2004/0076649 A1* | 4/2004 | Blin | A61K 8/02 424/401 |
| 2005/0002976 A1 | 1/2005 | Wu | |
| 2007/0060666 A1* | 3/2007 | Taniguchi | B65B 3/326 523/105 |
| 2010/0112019 A1* | 5/2010 | Thevenet | A61Q 1/02 424/401 |
| 2013/0058880 A1* | 3/2013 | Dong | A61K 8/28 424/63 |
| 2019/0053602 A1 | 2/2019 | Amari et al. | |

FOREIGN PATENT DOCUMENTS

| | | |
|---|---|---|
| EP | 0 523 964 A1 | 1/1993 |
| JP | 7-173031 A | 7/1995 |
| JP | 2003-506470 A | 2/2003 |
| JP | 2005-523981 A | 8/2005 |
| JP | 2006-104211 A | 4/2006 |
| JP | 2007-154336 A | 6/2007 |
| JP | 2007-526224 A | 9/2007 |
| JP | 4077035 B2 | 4/2008 |
| JP | 2008-179629 A | 8/2008 |

(Continued)

OTHER PUBLICATIONS

International Search Report dated Apr. 10, 2018 in PCT/JP2017/047079 filed on Dec. 27, 2017.
Safe Data Sheet (SDS), [online], Showa Chemical Co., Ltd., Internet <URL: http://www.st.rim.or.jp/-shw/MSDS22033350.pdf>, 10 pages (with unedited computer-generated English translation).
Extended European Search Report dated Jul. 21, 2020 in Patent Application No. 17886241.3, 8 pages.

*Primary Examiner* — Tigabu Kassa
(74) *Attorney, Agent, or Firm* — Oblon, McClelland, Maier & Neustadt, L.L.P.

(57) ABSTRACT

The coating formation method of the present invention is a method for forming a coating on a surface of a coating formation target. The formation method of the present invention includes an electrostatic spraying step of electrostatically spraying a composition directly onto the coating formation target, thereby forming a coating composed of a deposit containing fibers. The composition contains a component (a), a component (b), and a component (c) below. (a) One or more volatile substances selected from water, alcohols, and ketones. (b) A polymer having coating formability. (c) A liquid agent containing one or more selected from oils and polyols that are in a liquid form at 20° C.

9 Claims, 2 Drawing Sheets

(56) References Cited

FOREIGN PATENT DOCUMENTS

| | | |
|---|---|---|
| JP | 2017-78062 A | 4/2017 |
| JP | 2018-177724 A | 11/2018 |
| JP | 2018-177725 A | 11/2018 |
| KR | 2003-0096380 A | 12/2003 |
| WO | WO 94/11119 A1 | 5/1994 |
| WO | WO 98/03267 A1 | 1/1998 |
| WO | WO 01/12137 A1 | 2/2001 |
| WO | WO 01/12152 A2 | 2/2001 |
| WO | WO 2004/112744 A1 | 12/2004 |

* cited by examiner

[Fig.1]
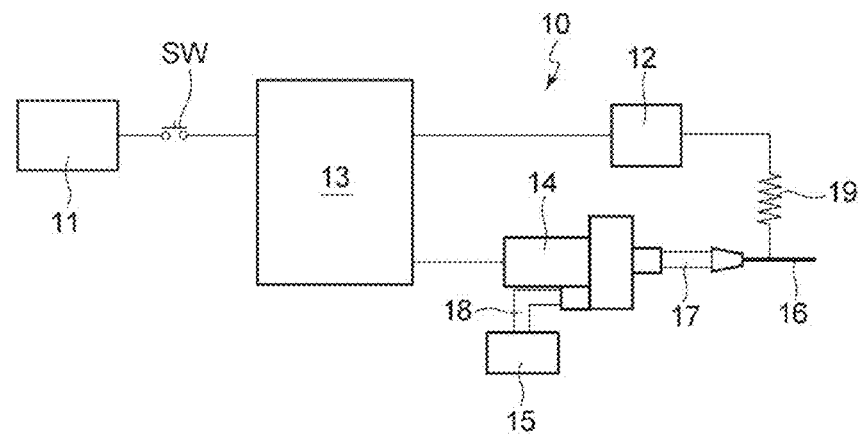
[Fig.2]
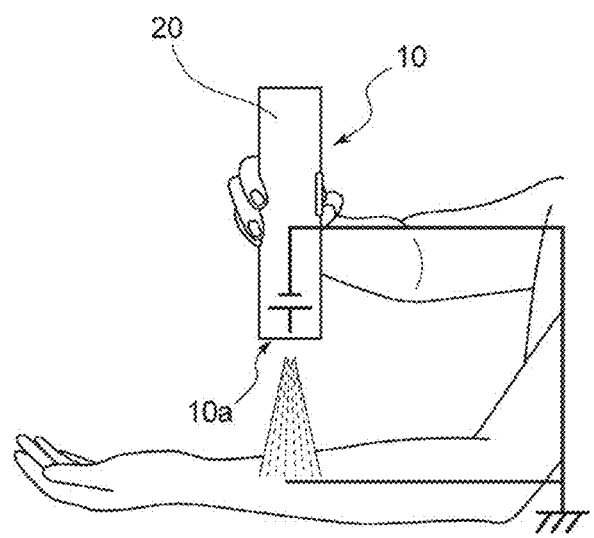

[Fig.3]
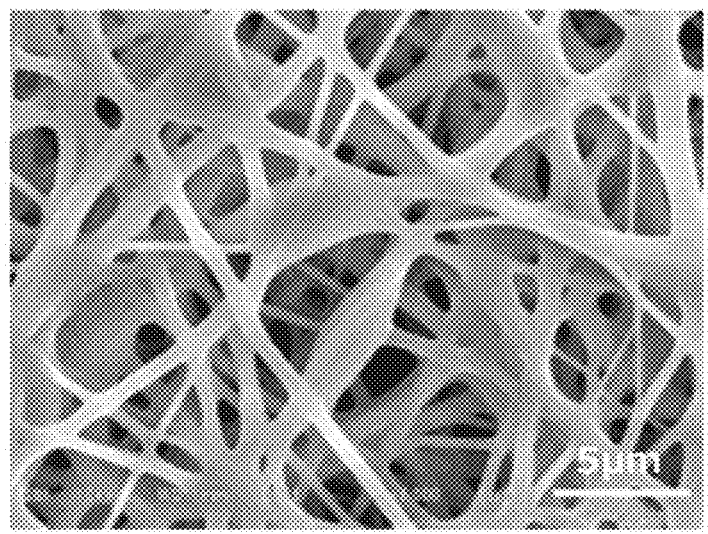
[Fig.4]
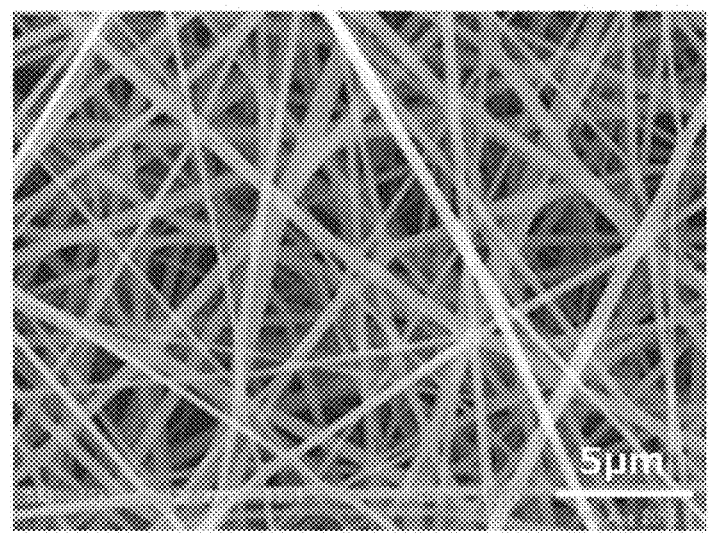

METHOD FOR MANUFACTURING COATING FILM BY ELECTROSTATIC SPRAYING

TECHNICAL FIELD

The present invention relates to a coating formation method.

BACKGROUND ART

A cosmetic sheet containing cosmetics or cosmetic components in order to enable cosmetics, cosmetic components, or medicinal products for external wounds to effectively act on skin is described, for example, in Patent Literature 1. Furthermore, for example, Patent Literatures 2 and 3 describe methods for forming a coating through electrostatic spraying.

CITATION LIST

Patent Literatures

Patent Literature 1: JP 2008-179629A
Patent Literature 2: U.S. Pat. No. 6,531,142(B1)
Patent Literature 3: WO 9803267(A1)

SUMMARY OF INVENTION

The present invention is directed to a coating formation method for forming a coating on a surface of a coating formation target. The coating formation method includes an electrostatic spraying step of electrostatically spraying a composition directly onto the coating formation target, thereby forming a coating composed of a deposit containing fibers. The composition contains a component (a), a component (b), and a component (c) below. (a) One or more volatile substances selected from water, alcohols, and ketones. (b) A polymer having coating formability. (c) A liquid agent containing one or more selected from oils and polyols that are in a liquid form at 20° C.

BRIEF DESCRIPTION OF DRAWINGS

FIG. 1 is a schematic view showing the configuration of an electrostatic spraying apparatus that is preferably used in the present invention.

FIG. 2 is a schematic view showing a state in which an electrostatic spraying method is performed using the electrostatic spraying apparatus.

FIG. 3 shows an SEM image of a coating of Example 3.

FIG. 4 shows an SEM image of a coating of Comparative Example 1.

DESCRIPTION OF EMBODIMENTS

The cosmetic sheet described in Patent Literature 1 contains cosmetics or cosmetic components, and thus it is possible to enable cosmetics or the like to effectively act on skin. However, the cosmetic sheet described in Patent Literature 1 is a sheet that is produced in advance and then is made to contain cosmetics or the like, and thus, the sheet is likely to come off the target from an edge thereof when worn if a frictional force is applied thereto. Furthermore, if the sheet produced in advance is stored in a state in which its fibers contain not only cosmetics or the like but also non-volatile oils such as almond oil, avocado oil, or olive oil, or polyols, the fiber shape of constituent fibers of the sheet is likely to collapse, the sheet form is likely to collapse, and the storage stability is poor.

The method for treating skin through electrostatic spraying described in Patent Literature 2 is a method in which skin is treated by electrostatically spraying particles composed of a particulate powder material. That is to say, the coating is not a deposit of fibers and is thus unlikely to remain in the form of a single film, and thus there is a reduction in the durability such as partial detachment of the particles when in use, for example, and the coating is difficult to take off after use.

On the other hand, according to the method for forming a coating through electrostatic spraying described in Patent Literature 3, the coating that is formed is a deposit of fibers and thus can be treated as a single film, and thus the coating is easy to take off after use. However, the adhesion between the coating formed through electrostatic spraying and a substrate is insufficient, and thus the coating may be damaged or come off due to an external force such as friction. Moreover, there is no description in Patent Literature 3 regarding forming a transparent coating composed of a deposit of fibers, thereby coating skin in a natural state.

Thus, the present invention relates to a coating formation method that can solve the above-described disadvantages of conventional techniques.

Hereinafter, the present invention will be described based on a preferred embodiment thereof with reference to the drawings. The formation method of the present invention is a coating formation method for forming a coating on a surface of a coating formation target. In this embodiment, a coating is formed by directly applying a composition containing predetermined components to a human skin surface that is an example of the coating formation target. In the present invention, an electrostatic spraying method is used as a method for forming a coating. The electrostatic spraying method is a method in which a positive or negative high voltage is applied to a composition to electrify the composition, and then the electrified composition is sprayed onto a coating formation target. The sprayed composition spreads in a space while being repeatedly micronized due to Coulomb repulsion, and during this process or after the composition has attached to the coating formation target, a solvent that is a volatile substance dries to form a coating on the surface of the coating formation target.

The composition used in the present invention (this composition is also referred to as a "spray composition" hereinafter) is in a liquid form in an environment where the electrostatic spraying method is performed (e.g., 20° C.). This composition contains a component (a), a component (b), and a component (c) below:

(a) one or more volatile substances selected from water, alcohols, and ketones;

(b) a polymer having coating formability: and (c) a liquid agent containing one or more selected from oils and polyols that are in a liquid form at 20° C.

The spray composition is used in a coating formation method for forming a transparent or translucent coating composed of a deposit containing fibers, on human skin that is an example of the coating formation target, using the electrostatic spraying method.

Hereinafter, each composition will be described.

A volatile substance to be used as the component (a) is a substance having volatility in a liquid form. The component (a) is blended into the spray composition for the ultimate purpose of forming a dry coating in the following manner: when the spray composition that has been placed in an electric field and sufficiently electrified is discharged from the tip of a nozzle onto, for example, skin that is a coating formation target, the charge density of the spray composition becomes excessive as the component (a) evaporates, and then the component (a) further evaporates while the spray composition is further micronized due to Coulomb repulsion. For this purpose, the vapor pressure of the volatile substance at 20° C. is preferably from 0.01 kPa to 106.66 kPa, more preferably from 0.13 kPa to 66.66 kPa, even more preferably from 0.67 kPa to 40.00 kPa. and even more preferably from 1.33 kPa to 40.00 kPa.

Preferable examples of alcohols serving as the volatile substance to be used as the component (a) include chain aliphatic monohydric alcohols, cyclic aliphatic monohydric alcohols, and aromatic monohydric alcohols. Specific examples thereof include ethanol, isopropyl alcohol, butyl alcohol, phenylethyl alcohol, propanol, and pentanol. One or more alcohols selected from these alcohols can be used.

Examples of ketones serving as the volatile substance to be used as the component (a) include acetone, methyl ethyl ketone, and methyl isobutyl ketone. These ketones can be used alone or in combination of two or more.

The volatile substance to be used as the component (a) is more preferably one or more selected from ethanol, isopropyl alcohol, butyl alcohol and water, even more preferably one or more selected from ethanol and butyl alcohol, and even more preferably ethanol. Furthermore, if a later-described component (b) is a water-insoluble polymer, the volatile substance to be used as the component (a) is a mixed liquid preferably containing (a1) one or more selected from ethanol, isopropyl alcohol, and butyl alcohol, from the viewpoint of dispersibility of the component (b), and preferably (a2) water, from the viewpoint of providing electric charge. The mass ratio (a2)/(a1) between the component (a2) and the component (a1) is preferably from 0.0025 to 0.3, from the viewpoint of forming fibers using the spray composition and the adhesion of the coating.

The spray composition contains, along with the component (a), a polymer having coating formability to be used as the component (b). The polymer having coating formability to be used as the component (b) is generally a substance that can be dissolved in the volatile substance to be used as the component (a). The term "dissolve" as used herein refers to a state in which a substance is in a dispersed state at 20° C. and the dispersion is uniform when visually observed, and preferably transparent or translucent when visually observed.

As the polymer having coating formability, a polymer is used that is appropriate according to the properties of the volatile substance to be used as the component (a). Specifically, polymers having coating formability are roughly classified into water-soluble polymers and water-insoluble polymers. The term "water-soluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, 0.5 g or more of the immersed polymer dissolves in the water. On the other hand, the term "water-insoluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, more than 0.5 g of the immersed polymer does not dissolve in the water. The polymer having coating formability preferably contains a water-insoluble polymer.

Examples of the polymers that have coating formability and that are water-insoluble include: naturally-occurring macromolecules such as pullulan, hyaluronic acid, chondroitin sulfate, poly-γ-glutamic acid, modified corn starch, 3-glucan, glucooligosaccharide, heparin, mucopolysaccharide such as keratosulfate, cellulose, pectin, xylan, lignin, glucomannan, galacturonic acid, psyllium seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose, and hydroxypropyl methyl cellulose; and synthetic macromolecules such as partially saponified polyvinyl alcohol (when not used in combination with a cross-linking agent), low saponified polyvinyl alcohol, polyvinyl pyrrolidone (PVP), polyethylene oxide, and sodium polyacrylate. These water-soluble polymers can be used alone or in combination of two or more. It is preferable to use pullulan and synthetic macromolecules such as partially saponified polyvinyl alcohol, low saponified polyvinyl alcohol, polyvinyl pyrrolidone, and polyethylene oxide, of these water-soluble polymers, from the viewpoint of forming a coating with ease. When polyethylene oxide is used as the water-soluble polymer, its number average molecular weight is preferably from 50,000 to 3,000,000, and more preferably from 100,000 to 2,500,000.

On the other hand, examples of the water-insoluble polymers having coating formability include completely saponified polyvinyl alcohol, which can be insolubilized after formation of a coating; partially saponified polyvinyl alcohol, which can be cross-linked after formation of a coating when used in combination with a cross-linking agent; oxazoline modified silicone such as a poly(N-propanoylethyleneimine)-grafted dimethylsiloxane/γ-aminopropylmethylsiloxane copolymer; polyvinylacetal diethylamino acetate; zein (main component of corn proteins): polyester; polylactic acid (PLA): an acrylic resin such as a polyacrylonitrile resin and a polymethacrylic acid resin: a polystyrene resin; a polyvinyl butyral resin; a polyethylene terephthalate resin: a polybutylene terephthalate resin: a polyurethane resin; a polyamide resin; a polyimide resin; and a polyamideimide resin. These water-insoluble polymers can be used alone (one) or in combination of two or more. It is preferable to use completely saponified polyvinyl alcohol, which can be insolubilized after formation of a coating, partially saponified polyvinyl alcohol, which can be cross-linked after formation of a coating when used in combination with a cross-linking agent, a polyvinyl butyral resin, an acrylic resin such as an (alkyl acrylate/octylamide) copolymer, oxazoline modified silicone such as a poly(N-propanoylethyleneimine)-grafted dimethylsiloxane/γ-aminopropylmethylsiloxane copolymer, polyester, zein, and the like, of these water-insoluble polymers.

The spray composition contains, along with the component (a) and the component (b), a liquid agent containing one or more selected from oils and polyols that are in a liquid form at 20° C. to be used as the component (c). The component (c) is preferably non-volatile in a liquid state. Similarly to the polymer to be used as the component (b), the component (c) is generally a substance that can be dissolved in the volatile substance to be used as the component (a). The term "dissolve" as used herein refers to a state in which a substance is in a dispersed state at 20° C. and the dispersion is uniform when visually observed, and preferably transparent or translucent when visually observed.

As the oil that is in a liquid form at 20° C. to be used as the component (c), an oil is used that is appropriate according to the properties of the volatile substance to be used as the component (a). Examples of the oil include hydrocarbon oils, ester oils, silicone oils, and higher alcohols that are in a liquid form at 20° C. and liquid oils selected therefrom can be used alone or in combination of two or more. In the present invention, an oil that is in a liquid form at 20° C. is also referred to as a "liquid oil". Examples of the ester oils include, along with oils such as triacylglyceride (triglycerin fatty acid ester) contained in plant oils, compounds having an ester structure with an HLB value of 10 or less. The HLB value is an indicator indicating hydrophile lipophile balance, and, in the present invention, is a value calculated using the following formula of Oda, Teramura, et al.

$$HLB = (\Sigma \text{ inorganicity value} / \Sigma \text{ organicity value}) \times 10$$

The component (c) preferably contains an oil that is in a liquid form at 20° C., from the viewpoint of improving the adhesion of the polymer to be used as the component (b) to a coating formation target, and preferably contains one or more selected from ester oils and higher alcohols, and one or more selected from ester oils, from the viewpoint of providing polarity and improving the adhesion of the polymer to be used as the component (b) to a coating target.

Examples of the hydrocarbon oils that are in a liquid form at 20° C. described above as the component (c) include liquid paraffin, squalane, squalene, n-octane, n-heptane, cyclohexane, light isoparaffin, and liquid isoparaffin, and liquid paraffin and squalane are preferable from the viewpoint of improving usability. The viscosities of the hydrocarbon oils at 30° C. are preferably 10 mPa·s or more, and more preferably 30 mPa·s or more, from the viewpoint of bringing the electrostatically sprayed coating into intimate contact with the skin. From these viewpoints, the total content of isododecane, isohexadecane, and hydrogenated polyisobutene that have a viscosity of less than 10 mPa·s at 30° C., in the spray composition, is preferably 10% by mass or less, more preferably 5% by mass or less, even more preferably 1% by mass or less, and even more preferably 0.5% by mass or less, or alternatively, none of these oils need to be contained in the spray composition. Here, the viscosity is measured using a BM type viscometer (manufactured by Tokimec Inc.; measurement condition: rotor No. 1, 60 rpm, 1 minute) at 30° C. Note that, since the component (c) is in a liquid form at 20° C., the upper limit of the viscosity at 30° C. is not limited as long as the component (c) can flow, and is preferably 2000 mPa·s or less.

Examples of the ester oils that are in a liquid form at 20° C. described above as the component (c) include an ester compound with an HLB value of 10 or less, such as fatty acid esters, fatty acid alcohol esters, polyhydric alcohol esters, glycerin fatty acid esters, polyglycerin fatty acid esters, and sorbitan fatty acid esters, and these ester oils can be used alone or in combination of two or more. Examples of the glycerin fatty acid esters include monoglycerin fatty acid esters, diglycerin fatty acid esters, and triglycerin fatty acid esters.

Examples of the ester oils that are in a liquid form at 20° C. described above as the component (c) include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrite tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalene dicarboxylate, (12- to 15-carbon) alkyl benzoate, isononyl isononanoate, cetearylisononanoate, glycerin tri(caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, glyceryl tri-coconut-oil fatty acid, glyceryl trioleate, glyceryl trilinoleate, castor oil fatty acid methyl ester, oleyl oleate, 2-heptylundecyl palmitate, diisobutyl adipate, N-lauroyl-L-glutamate-2-octyldodecyl ester, di-2-heptylundecyl adipate, ethyllaurate, isobutyl adipate, diethyl sebacate, di-2-ethylhexyl sebacate, 2-hexyldecyl myristate, 2-hexyldecyl palmitate. 2-hexyldecyl adipate, diisopropyl sebacate, di-2-ethylhexyl succinate, triethyl citrate, 2-ethylhexyl p-methoxycinnamate, and tripropylene glycol dipivalate.

Of these, from the viewpoint of bringing the electrostatically sprayed coating into intimate contact with skin, and improving the tactile feel when the spray is applied to the skin, at least one (one or more) selected from octyldodecyl myristate, myristyl myristate, isocetyl stearate, isocetyl isostearate, cetearylisononanoate, isobutyl adipate, diethyl sebacate, di-2-ethylhexyl sebacate, isopropyl myristate, isopropyl palmitate, diisostearyl malate, neopentyl glycol dicaprate, (12- to 15-carbon) alkyl benzoate, isononyl isononanoate, glycerin tri(caprylate/caprate), and triacylglyceride containing a fatty acid such as oleic acid, stearic acid, palmitic acid, eicosenoic acid, icosenoic acid, or docosenoic acid is preferable, and one or more selected from isopropyl myristate, isopropyl palmitate, diisostearyl malate, diethyl sebacate, neopentyl glycol dicaprate, (12- to 15-carbon) alkyl benzoate, isononyl isononanoate, glycerin tri(caprylate/caprate), and triacylglyceride containing or more selected from oleic acid, eicosenoic acid, icosenoic acid, and docosenoic acid are preferable.

It is also possible to use plant oils such as olive oil, jojoba oil, macadamia nut oil, meadowfoam oil, castor oil, safflower oil, sunflower oil, avocado oil, canola oil, apricot kernel oil, rice germ oil, or rice bran oil, including the above-described ester oils such as triglycerides, or animal oils including lanolin or the like.

Examples of the polyglycerin fatty acid ester included in the ester oils that are in a liquid form at 20° C. described above as the component (c) include polyglyceryl isostearate, polyglyceryl diisostearate, polyglyceryl triisostearate, polyglyceryl stearate, polyglyceryl oleate, and polyglyceryl sesquicaprate, with an HLB value of 10 or less. Furthermore, examples of the sorbitan fatty acid ester include sorbitan monostearate, sorbitan monooleate, sorbitan sesquioleate, sorbitan sesquiisostearate, sorbitan monopalmitate, sorbitan tristearate, sorbitan trioleate, and sorbitan coconut-oil fatty acid, with an HLB value of 10 or less.

Of these, from the viewpoint of bringing the electrostatically sprayed coating into intimate contact with skin, and improving the tactile feel when the spray is applied to the skin, polyglyceryl isostearate, polyglyceryl diisostearate, polyglyceryl triisostearate, polyglyceryl stearate, polyglyceryl oleate, and polyglyceryl sesquicaprate are preferable, and polyglyceryl diisostearate is more preferable.

Examples of the silicone oils that are in a liquid form at 20° C. described above as the component (c) include dimethylpolysiloxane, dimethyl cclopolysiloxane, methylphenylpolysiloxane, methylhydrogenpolysiloxane, and higher alcohol modified organopolysiloxane. From the viewpoint of improving the adhesion to skin and the like, the spray composition of the present invention is such that the content of the silicone oil in the spray composition is preferably 10% by mass or less, and more preferably 7% by mass or less, and is preferably 0.1% by mass or more, and more preferably 1% by mass or more. The silicone oil does not have to be contained in the spray composition of the present invention, and, in this case, the content is preferably 5% by mass or less, more preferably 1% by mass or less, and even more preferably 0.1% by mass or less.

The kinetic viscosity at 25° C. of the silicone oil is preferably 3 mm²/s or more, more preferably 4 mm²/s or more, and even more preferably 5 mm²/s or more, and preferably 30 mm²/s or less, more preferably 20 mm²/s or less, and even more preferably 10 mm²/s or less, from the viewpoint of bringing the electrostatically sprayed coating into intimate contact with skin and the like. Of these, from the viewpoint of bringing the electrostatically sprayed coating into intimate contact with skin and the like, the silicone oil preferably contains dimethylpolysiloxane.

Examples of the higher alcohols that are in a liquid form at 20° C. described above as the component (c) include liquid higher alcohols with 12 to 20 carbon atoms, wherein higher alcohols of branched fatty acids or unsaturated fatty acids are preferable, and isostearyl alcohol and oleyl alcohol are more preferable.

If the component (c) is a polyol, a polyol is used that is appropriate according to the properties of the volatile substance to be used as the component (a). Specifically, examples of the polyol include alkylene glycols such as ethylene glycol, propylene glycol. 1,3-propanediol, and 1,3-butanediol; polyalkylene glycols such as diethylene glycol, dipropylene glycol, polyethylene glycol with a number average molecular weight of 1000 or less, and polypropylene glycol: glycerins or polyglycerins such as glycerin, diglycerin, and triglycerin; and polyglyceryls. Of these, from the viewpoint of improving usability, ethylene glycol, propylene glycol, 1,3-butanediol, dipropylene glycol, polyethylene glycol, glycerin, and diglycerin are preferable, and propylene glycol, 1,3-butanediol, glycerin, and dipropylene glycol are more preferable. Note that the number average molecular weight of the polyethylene glycol is more preferably 600 or less, and more preferably 400 or less.

The oils and polyols that are in a liquid form at 20° C. described above as examples of the component (c) can be used alone or in combination of two or more. The component (c) is preferably a plasticizer for a polymer having coating formability. As described above, the component (c) is preferably one or more substances selected from oils that are in a liquid form at 20° C. selected from hydrocarbon oils, ester oils, silicone oils, higher alcohols, and polyols selected from alkylene glycols, polyalkylene glycols, glycerins, and triglycerins.

The content of the component (a) in the spray composition is preferably 50% by mass or more, more preferably 55% by mass or more, and even more preferably 60% by mass or more. Also, the content is preferably 98% by mass or less, more preferably 96% by mass or less, and even more preferably 94% by mass or less. The content of the component (a) in the spray composition is preferably from 50% by mass to 98° 6 by mass, more preferably from 55% by mass to 96% by mass, and even more preferably from 60% by mass to 94% by mass. When the component (a) is blended into the spray composition in this proportion, the spray composition can sufficiently volatilize when the electrostatic spraying method is performed.

The spray composition in the present invention may contain solid or semi-solid oils, that is, oils other than the component (c), within a range that does not inhibit the effects of the present invention. From the viewpoint of improving the adhesion of the coating to a coating formation target, and making the spray composition stable, the content of oils other than the component (c) in the spray composition is preferably 10% by mass or less, more preferably 8% by mass or less, and even more preferably 6% by mass or less.

The content of the component (b) in the spray composition is preferably 2% by mass or more, more preferably 4% by mass or more, and even more preferably 6% by mass or more, from the viewpoint of setting the viscosity of the spray composition to a proper range, and adjusting the thickness of the fibers to a proper thickness. Also, the content is preferably 50% by mass or less, more preferably 45% by mass or less, and even more preferably 40% by mass or less. The content of the component (b) in the spray composition is preferably from 2% by mass to 50% by mass, more preferably from 4% by mass to 45% by mass, and even more preferably from 6% by mass to 40% by mass. When the component (b) is blended into the spray composition in this proportion, a desired coating can be successfully formed.

The content of the component (c) in the spray composition is preferably 0.5% by mass or more, more preferably 1.0% by mass or more, and even more preferably 1.5% by mass or more. Also, the content is preferably 30% by mass or less, more preferably 25% by mass or less, and even more preferably 20% by mass or less. The content of the component (c) in the spray composition is preferably from 0.5% by mass to 30% by mass, more preferably from 1% by mass to 25% by mass, and even more preferably from 1.5% by mass to 20% by mass. When the component (c) is blended into the spray composition in this proportion, the adhesion of a desired coating to a coating formation target can be improved.

The spray composition may contain only the above-described component (a), component (b), and component (c), or may contain other components in addition to the component (a), the component (b), and the component (c) within a range that does not inhibit the effects of the present invention. Examples of the other components include a coloring pigment, an extender pigment, a dye, a surfactant with an HLB value of more than 10, a UV protection agent, an aromatic substance, a repellent, an antioxidant, a stabilizer, an antiseptic, an antiperspirant, and various vitamins. Note that the use applications of these agents are not limited to those of the agents, and may be other use applications depending on the purposes, that is, for example, an antiperspirant may be used as an aromatic substance. Furthermore, the use applications may be combined, that is, for example, an antiperspirant may be used as an agent having the effects of an antiperspirant and an aromatic substance. If the spray composition contains other components, the blend proportion of the other components is preferably from 0.1% by mass to 30% by mass, and more preferably from 0.5% by mass to 20% by mass.

When the electrostatic spraying method is performed, the viscosity at 25° C. of the spray composition used in this method is preferably 1 mPa·s or more, more preferably 10 mPa's or more, and even more preferably 50 mPa·s or more. In addition, the viscosity at 25° C. is preferably 5,000 mPa·s or less, more preferably 2,000 mPa's or less, and even more preferably 1,500 mPa·s or less. The viscosity at 25° C. of the spray composition is preferably from 1 mPa·s to 5,000 mPa·s, more preferably from 10 mPa·s to 2.000 mPa·s, and even more preferably from 50 mPa·s to 1,500 mPa·s. When a spray composition having a viscosity in this range is used, a coating, specifically, a porous coating composed of a deposit of fibers, can be successfully formed using the electrostatic spraying method. From the viewpoint of improving both the adhesion and the tactile feel, the viscosity of the spray composition at 25° C. is more preferably from 50 mPa·s to 1000 mPa's. The formation of the porous coating is advantageous from the viewpoint of preventing skin from getting sweaty. The viscosity of the spray composition is measured at 25° C. using an E-type viscometer. An E-type viscometer manufactured by Tokyo Keiki Inc. can be used as the E-type viscometer, for example. For example, a rotor No. 43 can be used as a rotor. The conditions for measuring the viscosity, that is, the model number of a rotor, the number of rotations, the rotating time, and the like are determined in each E-type viscometer according to viscosity ranges.

The spray composition is sprayed directly onto, for example, human skin that is a coating formation target in the electrostatic spraying method. The electrostatic spraying method includes an electrostatic spraying step of electrostatically spraying the spray composition onto skin using an electrostatic spraying apparatus, thereby forming a coating. The electrostatic spraying apparatus includes: a container in which the composition is accommodated: a nozzle from which the composition is discharged; a supply device that supplies the composition accommodated in the container to the nozzle; and a power source that applies a voltage to the nozzle. Preferably, FIG. 1 is a schematic diagram illustrating a configuration of an electrostatic spraying apparatus to be preferably used in the present invention. An electrostatic spraying apparatus 10 shown in FIG. 1 includes a low-voltage power source 11. The low-voltage power source 11 can generate a voltage of several volts to a dozen or so volts. It is preferable that the low-voltage power source 11 is constituted by one or more batteries for the purpose of enhancing the portability of the electrostatic spraying apparatus 10. Also, when a battery is used as the low-voltage power source 11, there is an advantage in that the battery can be easily replaced as necessary. An AC adapter or the like can be used as the low-voltage power source 11 instead of the battery.

The electrostatic spraying apparatus 10 also includes a high-voltage power source 12. The high-voltage power source 12 is connected to the low-voltage power source 11 and includes an electronic circuit (not shown) that boosts a voltage generated by the low-voltage power source 11 to a high voltage. A voltage boosting electronic circuit usually includes a transformer, a capacitor, a semiconductor element, and the like.

The electrostatic spraying apparatus 10 further includes an auxiliary electric circuit 13. The auxiliary electric circuit 13 intervenes between the above-described low-voltage power source 11 and high-voltage power source 12 and has a function of adjusting the voltage of the low-voltage power source 11 to allow the high-voltage power source 12 to operate stably. Furthermore, the auxiliary electric circuit 13 has a function of controlling the rotation rate of a motor provided in a micro gear pump 14, which will be described later. The amount of spray composition supplied from a container 15 for the spray composition, which will be described later, to the micro gear pump 14 is controlled by controlling the rotation rate of the motor. A switch SW is installed between the auxiliary electric circuit 13 and the low-voltage power source 11, and the operation of the electrostatic spraying apparatus 10 can be started/stopped by turning on/off the switch SW.

The electrostatic spraying apparatus 10 further includes a nozzle 16. The nozzle 16 is made of a conductor including various conductors typified by metal or a non-conductor such as plastic, rubber, or ceramic and has a shape allowing the spray composition to be discharged from the tip of the nozzle. A minute space through which the spray composition flows and that extends in the longitudinal direction of the nozzle 16 is formed inside the nozzle 16. With regard to the size of the cross section of this minute space, the diameter thereof is preferably from 100 µm to 1,000 µm. The nozzle 16 is in communication with the micro gear pump 14 via a duct 17. The duct 17 may be a conductor or a non-conductor. The nozzle 16 is electrically connected to the high-voltage power source 12. This makes it possible to apply a high voltage to the nozzle 16. In this case, in order to prevent a case where excessive current flows when a human body is in direct contact with the nozzle 16, the nozzle 16 is electrically connected to the high-voltage power source 12 via a current limiting resistor 19.

The micro gear pump 14, which is in communication with the nozzle 16 via the duct 17, functions as a supply device for supplying the spray composition accommodated in the container 15 to the nozzle 16. The low-voltage power source 11 supplies power to the micro gear pump 14, so that the micro gear pump 14 can operate. The micro gear pump 14 is configured to supply a predetermined amount of the spray composition to the nozzle 16 under control of the auxiliary electric circuit 13.

The container 15 is connected to the micro gear pump 14 via a flexible duct 18. The spray composition is accommodated in the container 15. It is preferable that the container 15 is of an exchangeable cartridge-type.

The electrostatic spraying apparatus 10 configured as described above can be used as shown in FIG. 2, for example. FIG. 2 shows the hand-held electrostatic spraying apparatus 10 having dimensions allowing the apparatus to be held in one hand. In the electrostatic spraying apparatus 10 shown in this diagram, all of the members shown in the configuration diagram in FIG. 1 are accommodated in a cylindrical housing 20. The nozzle (not shown) is arranged at one end 10a in the longitudinal direction of the housing 20. The nozzle is arranged in the housing 20 such that the direction in which the composition is discharged matches the longitudinal direction of the housing 20 and the nozzle projects toward the skin that is a coating formation target. Since the tip of the nozzle is arranged so as to project toward the coating formation target in the longitudinal direction of the housing 20, the spray composition is less likely to adhere to the housing, and the coating can be stably formed.

If the coating formation target is the user's skin, when the electrostatic spraying apparatus 10 is operated, a user, that is, a person who forms a coating on his/her skin through electrostatic spraying, holds the apparatus 10 in one hand and directs the one end 10a of the apparatus 10 at which the nozzle (not shown) is arranged toward a portion to be subjected to electrostatic spraying. FIG. 2 shows a state in which the one end 10a of the electrostatic spraying apparatus 10 is directed to the inner side of a forearm of the user. Under these conditions, the apparatus 10 is switched on to perform the electrostatic spraying method. When the apparatus 10 is turned on, an electric field is generated between the nozzle and the skin. In the embodiment shown in FIG. 2, a high positive voltage is applied to the nozzle, and the skin serves as a negative electrode. When the electric field is generated between the nozzle and the skin, the spray composition at the tip of the nozzle is polarized by electrostatic induction, thus shaping the tip of the spray composition into a cone shape. Then, electrified droplets of the spray composition are discharged to the air from the tip of the cone toward the skin along the electric field. When the component (a) used as a solvent evaporates from the electrified spray composition, which has been discharged to the air, the charge density of the surface of the spray composition becomes excessive, and the spray composition spreads in the space while being repeatedly micronized due to Coulomb repulsion and then reaches the skin. In this case, by appropriately adjusting the viscosity of the spray composition, it is possible to cause the sprayed composition to reach the skin in the state in which the composition is in a droplet form. Alternatively, while the composition is being discharged to the space, it is also possible to evaporate the component (a) that is a volatile substance used as a solvent from the composition, solidify the polymer having coating formability used as a solute to form fibers while the fibers are stretched and deformed due to an electric potential difference, and deposit the fibers on the skin surface. When the viscosity of the spray composition is increased, for example, it is easy to deposit the composition in a fibrous form on the skin surface. Accordingly, a coating composed of a deposit of fibers is formed on the skin surface. The coating composed of the deposit of fibers can also be formed by adjusting the distance between the nozzle and the skin, or the voltage applied to the nozzle.

A high electric potential difference is generated between the nozzle and the skin that is a coating formation target while the electrostatic spraying method is being performed. However, an impedance is very large, and therefore, a current flowing in a human body is extremely small. The inventors of the present invention confirmed that a current flowing in a human body while the electrostatic spraying method is being performed is smaller by several digits than a current flowing in a human body due to static electricity generated in everyday life, for example.

When the deposit of fibers is formed using the electrostatic spraying method, the thickness of the fibers expressed as a diameter of a corresponding circle is preferably 10 nm or more, and more preferably 50 nm or more. In addition, the thickness is preferably 3.000 nm or less, and more preferably 1,000 nm or less. The thickness of the fibers can be measured by observing the fibers magnified 10,000 times using a scanning electron microscope (SEM), for example, removing defects (mass of fibers, intersection of fibers, and droplets) from the two-dimensional images of the fibers, selecting any ten fibers, drawing a line orthogonal to the longitudinal direction of each of the fibers, and reading the diameter of the fiber directly.

The coating composed of a deposit of fibers formed using the electrostatic spraying method has, on the surface side of the fibers forming the coating, a liquid agent holding coating in which the component (c) is present. The surface side of the fibers refers to the surface, part of the surface, or a portion between the fibers. A content of the component (c) in the spray composition of approximately 1% by mass or more makes the constituent fibers swell although this depends on the affinity between a polymer and the component (c), and thus the fibers become soft and can better follow skin, and furthermore, bleeding out of the component (c) from the constituent fibers is likely to occur, and the liquid agent holding coating is likely to be formed between the constituent fibers, whereas a content of the component (c) in the spray composition of less than 1% by mass makes it difficult to form the liquid agent holding coating on the surface of the constituent fibers. If the liquid agent holding coating is formed on the fibers included in the coating in this way, the adhesion to skin that is a coating formation target is improved, the coating is likely to be more transparent, and the appearance appears more natural. In the present invention, a transparent or translucent coating refers to, for example, when the coating is formed on a coating formation target and, for example, if the coating target is human skin, a coating through which the color, preferably, fine patterns and the like of human skin that is the coating formation target can be seen, and a coating through which the color and the like of skin, preferably, fine structures such as crista cutis on skin are visible to the naked eye, wherein it is more preferable that the presence of the coating is unlikely to be noticed. Note that, if the coating is translucent, from the viewpoint of making the presence of the coating on a surface of a coating formation target unlikely to be noticed, the color of the coating is preferably white, and, for example, the L value when a transparent or white target is subjected to electrostatic spraying is preferably 80 or more, and more preferably 90 or more, and, from similar viewpoints, the a value and the b value are preferably from −20 to 30, more preferably from −10 to 20, and even more preferably from 0 to 10. The L value is a value as defined in CIE 1976 (L*,a*,b*) color space (CIELAB), where 100 indicates white, and 0 indicates black. Furthermore, since the durability of the adhesion is improved, the coating is effective in terms of moisturizing skin that is a coating formation target, or improving the state of the skin.

If the coating formation target is skin with sweat, sebum, and the like, containing the component (c) in the fibers results in the fibers being likely to swell and plasticize. For example, when thin films are formed by electrostatically spraying the same liquid agent composition for 5 seconds on a metal surface with no moisture or oil content and on a skin surface with moisture and oil content, for example, a palm of a hand, it is seen through time-series observation of a change in the fiber diameter that the diameter of the fibers electrostatically sprayed onto the skin surface increases over time through swelling more than that of the fibers electrostatically sprayed onto the metal surface. In this manner, if a coating containing fibers formed through electrostatic spraying is plasticized by oil content or moisture of skin and further softened, the fibers can better follow a skin texture, and bleeding out of a liquid agent, that is, the component (c) from the fibers occurs, so that the coating is present on the fiber surface or between the fibers, and thus the coating containing fibers becomes translucent or transparent, and the appearance appears more natural. If the coating formation target is skin with sweat, sebum, and the like, the fiber diameter due to swelling satisfies the formula (1) below.

$$\text{(Fiber diameter 30 seconds after spinning on skin)} > \text{(fiber diameter 30 seconds after spinning on metal plate)} \quad (1)$$

The mass ratio ((c)/((b)+(c))) of the component (c) relative to the total amount of the component (c) and the component (b) in the coating composed of a deposit of fibers formed using the electrostatic spraying method or the spray composition is preferably 0.05 or more, more preferably 0.08 or more, and even more preferably 0.1 or more, from the viewpoint of improving the adhesion of the coating and the appearance of the coating, and is preferably 0.75 or less, more preferably 0.7 or less, and even more preferably 0.55 or less, from the viewpoint of forming a coating through electrostatic spraying. From similar viewpoints, the mass ratio ((c)/((b)+(c))) of the component (c) relative to the total amount of the component (c) and the component (b) in the coating or the spray composition is preferably from 0.05 to 0.75, more preferably from 0.08 to 0.7, and even more preferably from 0.1 to 0.55. When the value of ((c)/((b)+ (c))) is within this range, the fibers are likely to be formed, the surface of the coating formed through electrostatic spraying is prevented from being sticky, and the tactile feel of the coating is improved.

The contents of the component (a), the component (b), and the component (c) included in the spray composition are measured as follows. The component (a) that is a volatile substance is not present in the formed coating, or evaporates even if present, and thus the measurement is performed in a state in which the formed coating contains only the component (b) and the component (c), and the contents are measured as follows.

<Method for Measuring the Contents of the Component (a), the Component (b), and the Component (c) Included in the Spray Composition>

The measurement is performed using a separation and identification method through liquid chromatography (HPLC) in a solution state, or an identification method through infrared spectroscopy (IR). In liquid chromatography, elution starts from components with a larger molecular weight, and thus the composition can be identified based on estimation of molecular weights and elution positions of the components. In IR analysis, functional groups can be assigned and identified using individual absorbent members, and, typically, identification is possible by comparing reference charts of commercially available additives and IR charts of the components.

<Method for Measuring the Contents of the Component (b) and the Component (c) in a Formed Coating>

Solvents in which coatings can be dissolved are searched for, and the coatings are dissolved in the solvents, after which a separation and identification method through liquid chromatography (HPLC) or an identification method through infrared spectroscopy (IR) is performed.

Although each fiber forming a coating is a continuous fiber with an infinite length in the formation principle, it is preferable that the fiber has a length at least 100 times longer than its thickness. For example, it is preferable that the formed coating contains fibers with a length of preferably 10 µm or more, more preferably 50 µm or more, and even more preferably 100 µm or more, and containing the component (b). In this specification, a fiber having a length over 100 times than its thickness is defined as a "continuous fiber". The cross-sectional shape of a fiber is preferably circular or elliptic, and the thickness of the fiber is the diameter if the cross-sectional shape is circular, and is the length of a major axis if the cross-sectional shape is elliptic. It is preferable that a coating formed using the electrostatic spraying method is a porous discontinuous coating composed of the deposit of one or more continuous fibers. Since the fibers are flexible and soft, the coating in such a form can be treated as one sheet composed of an aggregate and is characterized by being very soft, and therefore, there is an advantage in that the coating is unlikely to fall apart even when a shearing force is applied to the coating, and the ability of the coating to follow body movement is good. Furthermore, there is an advantage in that the coating can be completely taken off with ease. In contrast, a continuous coating having no pores is not easy to take off and has poor sweat diffusability, and thus the skin is likely to be sweaty. Furthermore, a porous discontinuous coating composed of a deposit of an aggregate of particles is difficult to completely take off without damaging the skin, because, for example, friction needs to be applied to the entire coating in order to completely take off the coating.

Moreover, according to the present invention, the spray composition contains the component (c), and thus the formed coating preferably includes binding portions in which fibers bind to each other at fiber intersections. If these binding portions are included, the ability of a coating that is formed on a skin surface to follow movement of the body including the skin is good, and the adhesion can be improved. The binding portions may be at a level where the fibers adhere to each other, or at a level where the fibers completely bind to each other. The binding portions can be seen in an SEM image.

In the electrostatic spraying step using the electrostatic spraying apparatus 10, the electrostatic sprayed fibrous spray composition directly reaches the skin in a state in which the component (a) is evaporating and the component (b) and the component (c) are electrified. Since the skin is also electrified as described above, the fibers in the form of a single film come into intimate contact with the skin due to an electrostatic force. Since there is fine unevenness such as that of skin texture on the skin surface, an anchor effect is obtained due to the unevenness, and the fibers in the form of a single film thus come into further intimate contact with the skin surface. After the electrostatic spraying is finished in this manner, the electrostatic spraying apparatus 10 is turned off. Accordingly, the electric field between the nozzle and the skin vanishes, and the electric charge on the skin surface is fixed. As a result, the coating in the form of a single film exhibits better adhesion, is unlikely to come off the target from an edge thereof when worn, and has improved durability when in use. Furthermore, since the fibers included in the coating contain the component (c), the coating can be sufficiently brought into intimate contact with skin even without additionally applying a liquid to the skin. The reason for this seems to be that, since the component (c) is present in the fibers, the fibers become soft due to a plasticizing effect and are better able to follow a surface with fine unevenness, and the fibers and the skin are cross-linked with the liquid due to bleeding out of the component (c) to the fiber surface. Furthermore, since a liquid agent holding coating in which the component (c) is present is formed between the fibers included in the coating or on the surface of the fibers, the fibers included in the coating are unlikely to reflect light, and the coating is likely to appear transparent, and can cover skin with a natural appearance.

Although the distance between the nozzle and the skin depends on the voltage applied to the nozzle, the distance of 50 mm to 150 mm is preferable in order to successfully form the coating. The distance between the nozzle and the skin can be measured using a commonly used non-contact sensor or the like.

Regardless of whether or not the coating formed using the electrostatic spraying method is a porous coating, the basis weight of the coating is preferably 0.1 $g/m^2$ or more, and more preferably 1 $g/m^2$ or more. In addition, the basis weight is preferably 50 $g/m^2$ or less, and more preferably 40 $g/m^2$ or less. For example, the basis weight of the coating is preferably from 0.1 $g/m^2$ to 50 $g/m^2$, and more preferably from 1 $g/m^2$ to 40 $g/m^2$. Setting the basis weight of the coating in this manner makes it possible to improve the adhesion of the coating.

In the description above, a coating is directly formed on skin that is a coating formation target, but the coating formation target may be a target other than skin, such as bodies of automobiles, stainless steel constituting built-in kitchens, or metal or ceramic portions of tableware. The coating formation target is not a base in the case in which a film is formed on the base and is then attached to the target as in conventional examples, but is a target on which a coating is directly formed through spraying. Accordingly, even in the case where a surface of the coating formation target is a surface with varying magnitudes in the rise and falls of the unevenness, a target where movement such as bending and stretching occurs, or a wavy surface, the coating of the present invention can have high adhesion and an excellent appearance. Examples of the coating formation target include tableware with curved or stepped portions, automobiles, walls with fine unevenness or pores, skin, nails, and the like, preferably include skin and nails, and more preferably include skin.

If the coating formation target is skin, the coating formation method of the present invention is useful as various beauty treatment methods that are not intended to be used as a method of operation, treatment, or diagnosis of a human body. For the purpose of beauty treatment, the coating formation method according to the present invention can be applied to whitening of skin, concealment of specks on skin, concealment of dullness/dark areas of skin, concealment of wrinkles of skin, shading of skin, protection of skin from ultraviolet rays, and moisturization of skin, for example. Alternatively, the coating formation method according to the present invention can also be applied to various actions for protecting skin that are domestically and individually performed, such as protecting various wounds including abrasions, cuts, lacerations, puncture wounds, and the like, and the prevention of bedsores. Thus, even when a coating is formed on a portion where the degree of expansion and contraction of skin is large such as a joint and a portion whose curvature is large such as a shoulder, the formed coating is unlikely to come off or break.

Although the present invention has been described based on the preferred embodiment above, the present invention is not limited to the above-mentioned embodiment. In the above-mentioned embodiment, a person who wants to form a coating on his/her skin holds the electrostatic spraying apparatus 10 and generates an electric field between the nozzle of the apparatus 10 and his/her skin, for example. However, a person who wants to form a coating on his/her skin need not hold the electrostatic spraying apparatus 10 as long as an electric field is generated between the nozzle and the skin. Furthermore, as shown in FIG. 2, the electrostatic spraying apparatus 10 is an apparatus that can be held by a human hand, but also may be an electrostatic spraying apparatus having an operation portion that includes a spray nozzle and that can be held by a human hand.

With respect to the above-described embodiment, the present invention further discloses the following aspects of the coating formation method.

<1>

A coating formation method for forming a coating on a surface of a coating formation target, comprising an electrostatic spraying step of electrostatically spraying a composition directly onto the coating formation target, thereby forming a coating composed of a deposit containing fibers, wherein the composition contains a component (a), a component (b), and a component (c) below: (a) one or more volatile substances selected from water, alcohols, and ketones: (b) a polymer having coating formability; and (c) a liquid agent containing one or more selected from oils and polyols that are in a liquid form at 20° C.

<2>

The coating formation method as set forth in clause <1>, wherein the coating has, on a surface side of the fibers forming the coating, a liquid agent holding coating in which the component (c) is present.

<3>

The coating formation method as set forth in clause <1> or <2>, wherein a mass ratio ((c)/((b)+(c))) of the component (c) relative to a total amount of the component (b) and the component (c) in the coating or a spray composition is preferably from 0.05 to 0.75, and more preferably from 0.08 to 0.7.

<4>

The coating formation method as set forth in clause <1> or <2>, wherein a mass ratio ((c)/((b)+(c))) of the component (c) relative to a total amount of the component (b) and the component (c) in the coating or a spray composition is preferably from 0.1 to 0.55.

<5>

The coating formation method as set forth in any one of clauses <1> to <4>, wherein the component (c) is one or more substances selected from hydrocarbon oils, ester oils, silicone oils, higher alcohols, and polyols.

<6>

The coating formation method as set forth in any one of clauses <1> to <5>, wherein, in the electrostatic spraying step, the composition is electrostatically sprayed onto the coating formation target using an electrostatic spraying apparatus, so that a coating composed of a deposit of fibers is formed, and the electrostatic spraying apparatus includes: a container in which the composition is accommodated; a nozzle from which the composition is discharged: a supply device that supplies the composition accommodated in the container to the nozzle: and a power source that applies a voltage to the nozzle.

<7>

The coating formation method as set forth in any one of clauses <1> to <6>, wherein a vapor pressure of the volatile substance to be used as the component (a) at 20° C. is from 0.01 kPa to 106.66 kPa, preferably from 0.13 kPa to 66.66 kPa, more preferably from 0.67 kPa to 40.00 kPa, and even more preferably from 1.33 kPa to 40.00 kPa.

<8>

The coating formation method as set forth in any one of clauses <1> to <7>, wherein the volatile substance to be used as the component (a) contains alcohol, preferably contains one or more selected from chain aliphatic monohydric alcohols, cyclic aliphatic monohydric alcohols, and aromatic monohydric alcohols, and more preferably contains one or more selected from ethanol, isopropyl alcohol, butyl alcohol, phenyl ethyl alcohol, propanol, and pentanol.

<9>

The coating formation method as set forth in any one of clauses <1> to <8>, wherein the volatile substance to be used as the component (a) is a mixed liquid of (a1) and (a2), and a mass ratio (a2)/(a1) between the component (a2) and the component (a1) is preferably from 0.0025 to 0.3, the (a1) is one or more selected from the group consisting of ethanol, isopropyl alcohol, and butyl alcohol, and the (a2) is water.

<10>

The coating formation method as set forth in any one of clauses <1> to <9>, wherein the volatile substance to be used as the component (a) contains ketone, and preferably contains one or more selected from acetone, methyl ethyl ketone, and methyl isobutyl ketone.

<11>

The coating formation method as set forth in any one of clauses <1> to <10>, wherein the volatile substance to be used as the component (a) is one or more selected from (a1) and (a2), the (a1) is one or more selected from the group consisting of ethanol, isopropyl alcohol, and butyl alcohol, the (a2) is water, and is preferably one or two selected from ethanol and butyl alcohol, and (a2) water, and is more preferably (a1) ethanol and (a2) water.

<12>

The coating formation method as set forth in any one of clauses <1> to <11>, wherein the polymer having coating formability contains a water-soluble polymer, and, preferably, the polymer having coating formability that is water-soluble is one or more selected from: naturally-occurring macromolecules such as pullulan, hyaluronic acid, chondroitin sulfate, poly-γ-glutamic acid, modified corn starch, β-glucan, glucooligosaccharide, heparin, mucopolysaccharide such as keratosulfate, cellulose, pectin, xylan, lignin, glucomannan, galacturonic acid, psyllium seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose, and hydroxypropyl methyl cellulose; partially saponified polyvinyl alcohol (not used in combination with a cross-linking agent); low saponified polyvinyl alcohol; polyvinyl pyrrolidone (PVP); polyethylene oxide; and sodium polyacrylate.

<13>

The coating formation method as set forth in any one of clauses <1> to <12>, wherein the polymer having coating formability to be used as the component (b) contains a water-insoluble polymer, and the polymer having coating formability that is water-insoluble is one or more selected from: completely saponified polyvinyl alcohol, which can be insolubilized after formation of a coating: partially saponified polyvinyl alcohol, which can be cross-linked after formation of a coating when used in combination with a cross-linking agent; oxazoline modified silicone; polyvinylacetal diethylamino acetate: zein; polyester; polylactic acid (PLA); a polyacrylonitrile resin: an acrylic resin; a polystyrene resin; a polyvinyl butyral resin; a polyethylene terephthalate resin; a polybutylene terephthalate resin; a polyurethane resin; a polyamide resin; a polyimide resin; and a polyamideimide resin, and, more preferably, the component (b) is a water-insoluble polymer.

<14>

The coating formation method as set forth in any one of clauses <1> to <13>, wherein the oil that is in a liquid form at 20° C. to be used as the component (c) is one or more selected from hydrocarbon oils, ester oils, silicone oils, and higher alcohols that are in a liquid form at 20° C., preferably one or more selected from ester oils and higher alcohols, and more preferably one or more selected from ester oils.

<15>

The coating formation method as set forth in any one of clauses <1> to <13>, wherein the component (c) is one or more selected from hydrocarbon oils, ester oils, silicone oils, and polyols.

<16>

The coating formation method as set forth in any one of clauses <1> to <14>, wherein the oil that is in a liquid form at 20° C. to be used as the component (c) is preferably one or more selected from hydrocarbon oils, ester oils, silicone oils, and higher alcohols that are in a liquid form at 20° C., and more preferably one or more selected from hydrocarbon oils, ester oils, and silicone oils that are in a liquid form at 20° C.

<17>

The coating formation method as set forth in any one of clauses <14> to <16>, wherein a hydrocarbon oil that is in a liquid form at 20° C. to be used as the component (c) is one or two selected from liquid paraffin, squalane, squalene, n-octane, n-heptane, cyclohexane, light isoparaffin, and liquid isoparaffin, and is preferably one or two selected from liquid paraffin and squalane.

<18>

The coating formation method as set forth in any one of clauses <14> to <17>, wherein a viscosity of the hydrocarbon oil at 30° C. is preferably 10 mPa·s or more, and more preferably 30 mPa·s or more.

<19>

The coating formation method as set forth in any one of clauses <1> to <18>, wherein a content of isododecane, isohexadecane, and hydrogenated polyisobutene that have a viscosity of less than 10 mPa·s at 30° C., in the composition, is preferably 10% by mass or less, more preferably 5% by mass or less, even more preferably 1% by mass or less, and even more preferably 0.5% by mass or less, or alternatively, the composition preferably contains none of isododecane, isohexadecane, and hydrogenated polyisobutene that have a viscosity of less than 10 mPa·s at 30° C.

<20>

The coating formation method as set forth in clause <14> or <16>, wherein the ester oil that is in a liquid form at 20° C. to be used as the component (c) is an ester compound with an HLB value of 10 or less, and is one or more selected from fatty acid ester, fatty acid alcohol ester, polyhydric alcohol ester, glycerin fatty acid ester, polyglycerin fatty acid ester, and sorbitan fatty acid ester.

<21>

The coating formation method as set forth in clause <20>, wherein the ester oil that is in a liquid form at 20° C. to be used as the component (c) is one or more selected from isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrite tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalene dicarboxylate, (12- to 15-carbon) alkyl benzoate, isononyl isononanoate, cetearylisononanoate, glycerin tri(caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, glyceryl tri-coconut-oil fatty acid, glyceryl trioleate, glyceryl trilinoleate, castor oil fatty acid methyl ester, oleyl oleate, 2-heptylundecyl palmitate, diisobutyl adipate, N-lauroyl-L-glutamate-2-octyldodecyl ester, di-2-heptylundecyl adipate, ethyllaurate, isobutyl adipate, diethyl sebacate, di-2-ethylhexyl sebacate, 2-hexyldecyl myristate. 2-hexyldecyl palmitate, 2-hexyldecyl adipate, diisopropyl sebacate, di-2-ethylhexyl succinate, triethyl citrate, 2-ethylhexyl p-methoxycinnamate, and tripropylene glycol dipivalate.

<22>

The coating formation method as set forth in clause <21>, wherein the fatty acid ester, the fatty acid alcohol ester, the polyhydric alcohol ester, and the glycerin fatty acid ester used as the ester oil that is in a liquid form at 20° C. to be used as the component (c) are preferably one or more selected from octyldodecyl myristate, myristyl myristate, isocetyl stearate, isocetyl isostearate, cetearylisononanoate, isobutyl adipate, diethyl sebacate, di-2-ethylhexyl sebacate, isopropyl myristate, isopropyl palmitate, diisostearyl malate, neopentyl glycol dicaprate, (12- to 15-carbon) alkyl benzoate, isononyl isononanoate, glycerin tri(caprylate/ caprate), and triacylglyceride, and more preferably one or more selected from isopropyl myristate, isopropyl palmitate, diisostearyl malate, diethyl sebacate, neopentyl glycol dicaprate, (12- to 15-carbon) alkyl benzoate, isononyl isononanoate, glycerin tri(caprylate/caprate), and triacylglyceride.

<23>

The coating formation method as set forth in clause <20>, wherein the polyglycerin fatty acid ester used as the ester oil that is in a liquid form at 20° C. to be used as the component (c) is one or more selected from polyglyceryl isostearate, polyglyceryl diisostearate, polyglyceryl triisostearate, polyglyceryl stearate, polyglyceryl oleate, and polyglyceryl sesquicaprate, with an HLB value of 10 or less, and is more preferably polyglyceryl diisostearate.

<24>

The coating formation method as set forth in clause <20>, wherein the sorbitan fatty acid ester used as the ester oil that is in a liquid form at 20° C. to be used as the component (c) is one or more selected from sorbitan monostearate, sorbitan monooleate, sorbitan sesquioleate, sorbitan sesquiisostearate, sorbitan monopalmitate, sorbitan tristearate, sorbitan trioleate, and sorbitan coconut-oil fatty acid, with an HLB value of 10 or less.

<25>

The coating formation method as set forth in clause <14> or <16>, wherein the silicone oil that is in a liquid form at 20° C. to be used as the component (c) is one or more selected from dimethylpolysiloxane, dimethylcyclopolysiloxane, methylphenylpolysiloxane, methylhydrogenpolysiloxane, and higher alcohol modified organopolysiloxane.

<26>

The coating formation method as set forth in clause <25>, wherein a content of the silicone oil in the composition is 10% by mass or less, preferably 5% by mass or less, more preferably 1% by mass or less, and even more preferably 0.1% by mass or less, a kinetic viscosity at 25° C. of the silicone oil is 3 mm$^2$/s or more, preferably 4 mm$^2$/s or more, and more preferably 5 mm$^2$/s or more, and 30 mm$^2$/s or less, preferably 20 mm$^2$/s or less, and more preferably 10 mm$^2$/s or less, and the silicone oil contains dimethylpolysiloxane.

<27>

The coating formation method as set forth in clause <14> or <16>, wherein the higher alcohol that is in a liquid form at 20° C. to be used as the component (c) is a liquid higher alcohol with 12 to 20 carbon atoms, and the higher alcohol is one or more selected from higher alcohols of branched fatty acids or unsaturated fatty acids, and is preferably one or two selected from isostearyl alcohol and oleyl alcohol.

<28>

The coating formation method as set forth in any one of clauses <1> to <27>, wherein the polyol to be used as the component (c) is one or more selected from ethylene glycol, propylene glycol, 1,3-propanediol, 1,3-butanediol, diethylene glycol, dipropylene glycol, polyethylene glycol with a number average molecular weight of 1000 or less, polypropylene glycol, glycerin, diglycerin, and triglycerin, is preferably one or more selected from ethylene glycol with a number average molecular weight of 600 or less, propylene glycol, 1,3-butanediol, dipropylene glycol, polyethylene glycol, glycerin, and diglycerin, and is more preferably one or more selected from propylene glycol, 1,3-butanediol, glycerin, and dipropylene glycol.

<29>

The coating formation method as set forth in any one of clauses <1> to <28>, wherein the oil and polyol that are in a liquid form at 20° C. to be used as the component (c) are one or more substances selected from oils that are in a liquid form at 20° C. selected from hydrocarbon oils, ester oils, silicone oils, higher alcohols, and polyols selected from alkylene glycols, polyalkylene glycols, glycerins, and triglycerins, and are preferably one or more selected from liquid paraffin, squalane, isopropyl myristate, isopropyl palmitate, diisostearyl malate, diethyl sebacate, neopentyl glycol dicaprate, (12- to 15-carbon) alkyl benzoate, isononyl isononanoate, glycerin tri(caprylate/caprate), triacylglyceride, polyglyceryl isostearate with an HLB value of 10 or less, polyglyceryl diisostearate, polyglyceryl triisostearate, polyglyceryl stearate, polyglyceryl oleate, polyglyceryl sesquicaprate, polyglyceryl isostearate, polyglyceryl diisostearate, polyglyceryl triisostearate, polyglyceryl stearate, polyglyceryl oleate, polyglyceryl sesquicaprate, dimethylpolysiloxane, ethylene glycol with a number average molecular weight of 600 or less, propylene glycol, 1,3-butanediol, dipropylene glycol, polyethylene glycol, glycerin, and diglycerin.

<30>

The coating formation method as set forth in any one of clauses <1> to <29>, wherein the component (a) contains (a1) ethanol and (a2) water, the component (b) is one or more selected from completely saponified polyvinyl alcohol, partially saponified polyvinyl alcohol, a polyvinyl butyral resin, an (alkyl acrylate/octylamide) copolymer, oxazoline modified silicone, polyester, and zein, and the component (c) is one or more selected from hydrocarbon oils, ester oils, silicone oils, and polyols.

<31>

The coating formation method as set forth in any one of clauses <1> to <29>, wherein the component (a) contains (a1) ethanol and (a2) water, the component (b) is one or more selected from a polyvinyl butyral resin, and an (alkyl acrylate/octylamide) copolymer, and the component (c) is one or more selected from hydrocarbon oils, ester oils, silicone oils, and polyols.

<32>

The coating formation method as set forth in any one of clauses <1> to <31>, wherein a content of the component (a) in the composition is preferably from 50% by mass to 98% by mass, more preferably from 55% by mass to 96% by mass, and even more preferably from 60% by mass to 94% by mass.

<33>

The coating formation method as set forth in any one of clauses <1> to <32>, wherein a content of oils other than the component (c) in the composition is preferably 10% by mass or less, more preferably 8% by mass or less, and even more preferably 6% by mass or less.

<34>

The coating formation method as set forth in any one of clauses <1> to <33>, wherein a content of the component (b) in the composition is preferably from 2% by mass to 50% by mass, more preferably from 4% by mass to 45% by mass, and even more preferably from 6% by mass to 40% by mass.

<35>

The coating formation method as set forth in any one of clauses <1> to <34>, wherein a content of the component (c) in the composition is preferably from 0.5% by mass to 30% by mass, more preferably from 1% by mass to 25% by mass, and even more preferably from 1.5% by mass to 20% by mass.

<36>

The coating formation method as set forth in any one of clauses <1> to <35>, wherein a content of the component (a)

in the composition is from 55% by mass to 96% by mass, a content of the component (b) is from 4% by mass to 45% by mass, and a content of the component (c) is from 1% by mass to 25% by mass, and more preferably from 1.5% by mass to 20% by mass.
<37>
The coating formation method as set forth in any one of clauses <1> to <36>,
wherein the composition contains only the component (a), the component (b), and the component (c), or contains other components in addition to the component (a), the component (b), and the component (c),
the other components are a coloring pigment, an extender pigment, a dye, a surfactant with an HLB value of more than 10, a UV protection agent, an aromatic substance, a repellent, an antioxidant, a stabilizer, an antiseptic, an antiperspirant, or various vitamins.
<38>
The coating formation method as set forth in clause <37>, wherein a blend proportion of the other components in the composition is from 0.1% by mass to 30% by mass, and preferably from 0.5% by mass to 20% by mass.
<39>
The coating formation method as set forth in any one of clauses <1> to <38>, wherein a viscosity at 25° C. of the composition is 1 mPa·s or more, preferably 10 mPa·s or more, and more preferably 50 mPa·s or more, and the viscosity at 25° C. is 5000 mPa·s or less, preferably 2000 mPa·s or less, and more preferably 1500 mPa·s or less, and is preferably from 1 mPa·s to 5000 mPa·s, more preferably from 10 mPa·s to 2000 mPa·s, and even more preferably from 50 mPa·s to 1500 mPa·s.
<40>
The coating formation method as set forth in any one of clauses <1> to <39>, wherein the coating formation target is a human skin surface.
<41>
The coating formation method as set forth in clause <40>, wherein the coating is transparent or translucent such that, after the coating is formed, a color of the skin can be seen through the coating.
<42>
The coating formation method as set forth in any one of clauses <1> to <41>, wherein the composition is in a liquid form at 20° C., and the fibers are formed by electrostatically spraying the liquid composition.
<43>
The coating formation method as set forth in any one of clauses <1> to <42>, wherein the fibers forming the coating are continuous fibers.
<44>
The coating formation method as set forth in any one of clauses <1> to <43>, wherein the coating includes binding portions at intersections of the fibers forming the coating.
<45>
A use of the composition for the coating formation method as set forth in any one of clauses <1> to <44>, wherein the coating formation target is human skin, and a transparent or translucent coating composed of a deposit containing fibers is formed on the skin through electrostatic spraying.
<46>
A use of the composition for forming a coating according to the electrostatic spraying as set forth in any one of clauses <1> to <44>, wherein the coating formation target is human skin.
<47>
The coating formation method as set forth in any one of clauses <1> to <44>, wherein an apparatus that is used for the electrostatic spraying is an electrostatic spraying apparatus that can be held by a human hand, or an electrostatic spraying apparatus having an operation portion that includes a spray nozzle and that can be held by a human hand.

EXAMPLES

Hereinafter, the present invention will be described more specifically by way of examples. However, the scope of the present invention is not limited to these examples. Unless otherwise stated, "%" means "% by mass".

Example 1

(1) Preparation of the Spray Composition
Ethanol (manufactured by Wako Pure Chemical Industries, Ltd.: product name Ethanol (99.5)) was used as the component (a) of the spray composition. Polyvinyl butyral (manufactured by Sekisui Chemical Co., Ltd.: product name S-LEC B BM-1) was used as the component (b) of the spray composition. Glycerin (manufactured by Kao Corporation: product name Concentrated glycerin (Cosmetic grade)) was used as the component (c) of the spray composition. The blend proportion in the spray composition is as shown in Tables 1 and 2. Note that the amounts of ethanol and glycerin shown in Tables 1 and 2 are effective amounts, and do not include water.
(2) Electrostatic Spraying Step
The electrostatic spraying method was performed directly onto skin for 20 seconds using the electrostatic spraying apparatus 10 having the configuration shown in FIG. 1 and the appearance shown in FIG. 2. The electrostatic spraying method was performed under the conditions described below.
  Applied voltage: 10 kV
  Distance between nozzle and skin: 100 mm
  Discharge amount of spray composition: 5 ml/h
  Environment: 25° C., 30% RH
A coating in the form of a single film composed of a deposit of fibers was formed on the skin surface through the electrostatic spraying. The coating had a circular shape with a diameter of about 4 cm, and had a mass of about 3.8 mg. The thickness of the fibers measured with the above-described method was 660 nm.

Examples 2 to 5

Coatings composed of a deposit of fibers were formed by performing the electrostatic spraying step as in Example 1, except that the components (a), (b), and (c) in the spray composition were changed to the conditions shown in Table 1 below.

Examples 6 to 101

Coatings composed of a deposit of fibers were formed by performing the electrostatic spraying step as in Example 1, except that the component (c) in the spray composition was changed to polyglyceryl-2 diisostearate (manufactured by the Nisshin OilliO Group, Ltd.: product name Cosmol 42V), and the conditions were changed to those shown in Table 1 below.

Example 11

Coatings composed of a deposit of fibers were formed by performing the electrostatic spraying step as in Example 1, except that the component (a) in the spray composition was changed to that obtained by adding 1-butanol (manufactured by Wako Pure Chemical Industries, Ltd.: product name 1 Butanol) to ethanol used in Example 1, the component (b) was changed to an (alkyl acrylate/octylacrylamide) copolymer (manufactured by Akzonobel: product name Dermacryl 79), the component (c) was changed to polyglyceryl-10 diisostearate (manufactured by Matsumoto Fine Chemical Co. Ltd.: product name Matsunate MI-102), and the conditions were changed to those shown in Table 1 below.

Comparative Example 1

A coating composed of a deposit of fibers was formed by performing the electrostatic spraying step as in Example 1, except that the spray composition did not contain the component (c).

Comparative Example 2

A coating composed of a deposit of fibers was formed by performing the electrostatic spraying step as in Example 1, except that the spray composition did not contain the component (c), the component (a) was changed to that obtained by adding 1-butanol (manufactured by Wako Pure Chemical Industries, Ltd.: product name 1Butanol) to ethanol used in Example 1, and the component (b) was changed to an (alkyl acrylate/octylacrylamide) copolymer (manufactured by Akzonobel: product name Dermacryl 79).

Evaluation

With regard to the coatings formed in the examples and comparative examples, the adhesion to skin, and the appearance of the coating were evaluated following the criteria below. Table 1 shows the results.

[Adhesion to Skin]

1: Immediately after spinning in the electrostatic spraying step, almost all the coating comes off.

2: The coating sticks to skin immediately after spinning in the electrostatic spraying step, but, after 30 minutes of being left in a still state, 50% or more of the area of the coating comes off.

3: The coating sticks to skin immediately after spinning in the electrostatic spraying step, but, after 30 minutes of being left in a still state, less than 50% of the area of the coating comes off.

4: The coating sticks to skin in a still state for 30 minutes after spinning in the electrostatic spraying step, but, when a shearing force is applied by a finger in the parallel direction, the coating comes off.

5: The coating sticks to skin in a still state for 30 minutes after spinning in the electrostatic spraying step, and, even when a shearing force is applied by a finger in the parallel direction, the coating does not come off.

[Appearance of the Coating]

1: The appearance of the coating looks white.

2: The appearance of the coating is translucent while almost being white.

3: The appearance of the coating looks translucent.

4: The appearance of the coating has a pale translucent color.

5: The appearance of the coating looks transparent.

TABLE 1

| | Component (a) (%) | | | Polyvinyl butyral | (Alkylacrylate/ octylacrylamide) copolymer | Component (c) (%) | |
|---|---|---|---|---|---|---|---|
| | Ethanol | 1-Butanol | Water | | | Glycerin | Polyglyceryl-2 diisostearate |
| Ex. 1 | 85.9 | | 0.4 | 13.0 | | 0.7 | |
| Ex. 2 | 85.2 | | 0.4 | 13.0 | | 1.4 | |
| Ex. 3 | 81.0 | | 0.5 | 13.0 | | 5.5 | |
| Ex. 4 | 74.0 | | 0.6 | 12.8 | | 12.6 | |
| Ex. 5 | 66.3 | | 0.7 | 10.0 | | 23.0 | |
| Ex. 6 | 85.9 | | 0.4 | 13.0 | | | 0.7 |
| Ex. 7 | 85.2 | | 0.4 | 13.0 | | | 1.4 |
| Ex. 8 | 81.0 | | 0.4 | 13.0 | | | 5.6 |
| Ex. 9 | 74.0 | | 0.4 | 12.8 | | | 12.8 |
| Ex. 10 | 66.4 | | 0.3 | 10.0 | | | 23.3 |
| Ex. 11 | 42.6 | 31.6 | 0.2 | 0 | 20.4 | | |
| Com. Ex. 1 | 86.6 | | 0.4 | 13.0 | | | |
| Com. Ex. 2 | 44.8 | 34.0 | 0.2 | | 21.0 | | |

| | Component (c) (%) | | Total | (C)/ ((B) + (C)) | (C)/coating | Evaluation | |
|---|---|---|---|---|---|---|---|
| | Polyglyceryl-10 diisostearate | Diethyl sebacate | | | | Adhesion | Appearance |
| Ex. 1 | | | 100.0 | 0.05 | 5% | 2 | 2 |
| Ex. 2 | | | 100.0 | 0.10 | 10% | 3 | 3 |
| Ex. 3 | | | 100.0 | 0.30 | 30% | 4 | 3 |
| Ex. 4 | | | 100.0 | 0.50 | 50% | 4 | 3 |
| Ex. 5 | | | 100.0 | 0.70 | 70% | 5 | 5 |
| Ex. 6 | | | 100.0 | 0.05 | 5% | 2 | 2 |
| Ex. 7 | | | 100.0 | 0.10 | 10% | 4 | 3 |
| Ex. 8 | | | 100.0 | 0.30 | 30% | 5 | 4 |
| Ex. 9 | | | 100.0 | 0.50 | 50% | 5 | 5 |

TABLE 1-continued

| | | | | | | |
|---|---|---|---|---|---|---|
| Ex. 10 | | 100.0 | 0.70 | 70% | 5 | 5 |
| Ex. 11 | 5.2 | 100.0 | 0.20 | 20% | 4 | 2 |
| Com. Ex. 1 | | 100.0 | 0.00 | 0% | 1 | 1 |
| Com. Ex. 2 | | 100.0 | 0.00 | 0% | 2 | 1 |

Example 12

The electrostatic spraying method was performed for 5 seconds on the targets (d) and (e) below through the electrostatic spraying step of Example 1 using the spray composition of Example 3. Coatings composed of a deposit of fibers 30 seconds after the adhesion were obtained.
(d) Palm of hand
(e) Surface of 100 mm×100 mm×10 mm aluminum metal plate Example 13

Coatings composed of a deposit of fibers were obtained by performing the electrostatic spraying step as in Example 12 using the spray composition of Example 7.

Example 14

Coatings composed of a deposit of fibers were obtained by performing the electrostatic spraying step as in Example 12, except that the components (a), (b), and (c) in the spray composition were changed to the conditions shown in Table 2 below.

Comparative Example 3

Coatings composed of a deposit of fibers were obtained by performing the electrostatic spraying step as in Example 12 through the electrostatic spraying step of Example 1 using the spray composition of Comparative Example 1.

Evaluation

After coatings were formed on the targets (d) and (e) through electrostatic spraying and left to adhere thereto for 30 seconds, the coatings were taken off, and their average fiber diameters were obtained by directly reading fiber diameters through observation using a scanning electron microscope (SEM). The thickness of the fibers was measured by observing the fibers magnified 10,000 times using a scanning electron microscope (SEM), removing defects (mass of fibers, intersection of fibers, and droplets) from the two-dimensional images of the fibers, selecting any ten fibers, drawing a line orthogonal to the longitudinal direction of each of the fibers, and reading the diameter of the fiber directly. If the formula (1) is satisfied, the adhesion to skin and the appearance of the coating are good, whereas, if the formula (2) is satisfied, the adhesion to skin is poor, and the appearance is white and unnatural. Table 2 shows the results.

$$\text{Average fiber diameter of } (d) > \text{Average fiber diameter of } (e) \quad (1)$$

$$\text{Average fiber diameter of } (d) \leq \text{Average fiber diameter of } (e) \quad (2)$$

TABLE 2

| | Component (a) (%) | | | Component (b) (%) | | Component (c) (%) | |
|---|---|---|---|---|---|---|---|
| | | | | Polyvinyl | (Alkylacrylate/ octylacrylamide) | | Polyglyceryl-2 |
| | Ethanol | 1-Butanol | Water | butyral | copolymer | Glycerin | diisostearate |
| Ex. 12 | 81.0 | | 0.5 | 13.0 | | 5.5 | |
| Ex. 13 | 85.2 | | 0.4 | 13.0 | | | 1.4 |
| Ex. 14 | 84.0 | | 0.4 | 14.0 | | | |
| Com. Ex. 3 | 86.6 | | 0.4 | 13.0 | | | |

| | Component (c) (%) | | | | | Average fiber diameter (nm) | |
|---|---|---|---|---|---|---|---|
| | Polyglyceryl-10 diisostearate | Diethyl sebacate | Total | (C)/((B) + (C)) | (C)/coating | Target (d) | Target (e) |
| Ex. 12 | | | 100.0 | 0.30 | 30% | 1077 | 1036 |
| Ex. 13 | | | 100.0 | 0.10 | 10% | 1408 | 915 |
| Ex. 14 | | 1.6 | 100.0 | 0.10 | 10% | 1116 | 974 |
| Com. Ex. 3 | | | 100.0 | 0.00 | 0% | 827 | 828 |

As is clear from the results shown in Tables 1 and 2, the coatings formed using the methods of the examples had higher adhesion to skin and higher transparency than those formed using the methods of the comparative examples.

Examples 15 to 28

Coatings composed of a deposit of fibers were obtained by performing the electrostatic spraying step as in Example 1 using the spray compositions shown in Tables 3 and 4. The adhesion to skin and the appearance of the coating were evaluated as in Example 1, and the tactile feel of the coating was evaluated as follows. Tables 3 and 4 show the results.

[Tactile Feel of the Coating]

With regard to the coatings of Examples 15 to 28, the tactile feel when the coatings 30 minutes after formation were pressed with a finger was evaluated following the criteria below. The evaluation was performed by three people, and Table 3 shows the results of their discussion.

1: Sticky
2: Somewhat significantly sticky
3: Moist tactile feel
4: Smooth
5: Smooth such that it feels slippery
-: Evaluation of adhesion is poorer than 5

TABLE 3

| | Component (a) | | Component (b) | Component (c) | | | | |
|---|---|---|---|---|---|---|---|---|
| | Ethanol | Water | Polyvinyl butyral | Dimethyl polysiloxane (*1) | Squalane | Liquid paraffin | Neopentyl glycol dicaprate (*2) | Jojoba oil |
| Ex. 15 | 81 | 0.4 | 13 | 5.6 | | | | |
| Ex. 16 | 81 | 0.4 | 13 | | 5.6 | | | |
| Ex. 17 | 81 | 0.4 | 13 | | | 5.6 | | |
| Ex. 18 | 81 | 0.4 | 13 | | | | 5.6 | |
| Ex. 19 | 81 | 0.4 | 13 | | | | | 5.6 |
| Ex. 20 | 81 | 0.4 | 13 | | | | | |
| Ex. 21 | 81 | 0.4 | 13 | | | | | |

| | Component (c) | | | | Evaluation | | |
|---|---|---|---|---|---|---|---|
| | Isononyl isononanoate (*3) | Dipropylene glycol | Total | (c)/((b) + (c)) | Adhesion | Appearance | Tactile feel |
| Ex. 15 | | | 100.0 | 30% | 4 | 3 | 4 |
| Ex. 16 | | | 100.0 | 30% | 4 | 3 | 4 |
| Ex. 17 | | | 100.0 | 30% | 4 | 3 | 4 |
| Ex. 18 | | | 100.0 | 30% | 4 | 4 | 4 |
| Ex. 19 | | | 100.0 | 30% | 4 | 3 | 4 |
| Ex. 20 | 5.6 | | 100.0 | 43% | 5 | 4 | 4 |
| Ex. 21 | | 5.6 | 100.0 | 30% | 5 | 4 | 4 |

(*1) KF-96A-63CS (manufactured by Shin-Etsu Chemical Co., Ltd.)
(*2) Estemol N-01 (manufactured by the Nisshin OilliO Group, Ltd.)
(*3) Salacos 99 (manufactured by the Nisshin OilliO Group, Ltd.)

TABLE 4

| | Component (a) | | | Component (b) | | Component (c) | |
|---|---|---|---|---|---|---|---|
| | Ethanol (a1) | 1-Butanol (a1) | Water (a2) | Polyvinyl butyral | (Alkylacrylate/ octylacrylamide) copolymer | Polyglyceryl-2 diisostearate | Polyglyceryl-10 diisostearate |
| Ex. 22 | 81 | | 0.4 | 13 | | 5.6 | |
| Ex. 23 | 74 | | 0.4 | 12.8 | | 12.8 | |
| Ex. 24 | 67.3 | | 0.4 | 10 | | 22.3 | |
| Ex. 25 | 42.6 | 31.6 | 0.2 | | 20.4 | | 5.2 |
| Ex. 26 | 71.8 | | 0.4 | 15 | | 12.8 | |
| Ex. 27 | 80.8 | | 0.4 | 6 | | 12.8 | |
| Ex. 28 | 69.8 | | 0.4 | 17 | | 12.8 | |

| | | | | Evaluation | | |
|---|---|---|---|---|---|---|
| | Total | (C)/((B) + (C)) | a2/a1 | Adhesion | Appearance | Tactile feel |
| Ex. 22 | 100.0 | 30% | 0.005 | 5 | 4 | 4 |
| Ex. 23 | 100.0 | 50% | 0.005 | 5 | 5 | 3 |
| Ex. 24 | 100.0 | 69% | 0.006 | 5 | 5 | 2 |
| Ex. 25 | 100.0 | 20% | 0.003 | 4 | 2 | — |
| Ex. 26 | 100.0 | 46% | 0.006 | 5 | 5 | 3 |
| Ex. 27 | 100 0 | 68% | 0.005 | 5 | 5 | 2 |
| Ex. 28 | 100.0 | 43% | 0.006 | 5 | 5 | 3 |

The viscosity of the spray compositions used to form the coatings of Examples 23 and 25 to 28 was measured under later-described conditions. Table 5 shows the measurement results of the viscosity, and the evaluation results of the adhesion and the tactile feel of the coatings of Examples 23 and 25 to 28.

The coatings of Examples 26 and 28 shown in Table 5 were coatings with high adhesion to skin and a moist tactile feel, but they had a somewhat significant tackiness, which seems to be a tactile feel due to the component (b) not being completely dried and a tackiness being expressed. On the other hand, the coating of Example 27 in which the content of the component (c) was larger than that of the component (b) was a coating with high adhesion to skin and a somewhat significant sticky tactile feel, which seems to be stickiness derived from the component (c).

The viscosity was measured under the following conditions: a spray composition was prepared and then stored for one day at 25° C., after which the viscosity was measured at 25° C. using an E-type viscometer (Visconic EMD, manufactured by Tokyo Keiki Inc.) with a rotor No. 43, where the number of rotations was set to 1 rpm for 1280 mPa·s or more, to 10 rpm for 128 mPa·s or more and less than 1280 mPa·s, and to 100 rpm for less than 128 mPa·s.

Example 29

A coating composed of a deposit of fibers was obtained by performing the electrostatic spraying step as in Example 1 using the spray composition shown in Table 6. The appearance of the coating was evaluated as in Example 1. Table 6 show the evaluation result.

TABLE 6

| | Component (a) | | Component (b) | Component (c) | | (C)/ | | Evaluation |
| | Ethanol (a1) | Water (a2) | Polyvinyl butyral | Glycerin | Total | ((B) + (C)) | a2/a1 | Appearance |
|---|---|---|---|---|---|---|---|---|
| Ex. 29 | 60 | 14 | 13 | 13 | 100.0 | 50% | 0.23 | 3 |

As is clear from the result shown in Table 6, the coating of Example 29 had a translucent appearance.

INDUSTRIAL APPLICABILITY

According to the present invention, the adhesion between a coating formation target and a coating formed through the electrostatic spraying can be increased, and the coating has a transparent appearance and can coat the coating formation target in a natural state.

TABLE 5

| | Component (a) | | | Component (b) | | Component (c) | |
| | Ethanol (a1) | 1-Butanol (a1) | Water (a2) | Polyvinyl butyral | (Alkylacrylate/ octylacrylamide) copolymer | Polyglyceryl-2 diisostearate | Polyglyceryl-10 diisostearate |
|---|---|---|---|---|---|---|---|
| Ex. 23 | 74 | | 0.4 | 12.8 | | 12.8 | |
| Ex. 25 | 42.6 | 31.6 | 0.2 | | 20.4 | | 5.2 |
| Ex. 26 | 71.8 | | 0.4 | 15 | | 12.8 | |
| Ex. 27 | 80.8 | | 0.4 | 6 | | 12.8 | |
| Ex. 28 | 69.8 | | 0.4 | 17 | | 12.8 | |

| | | | | Evaluation | | |
| | Total | (C)/((B) + (C)) | a2/a1 | Viscosity (mPa·s) | Adhesion | Tactile feel |
|---|---|---|---|---|---|---|
| Ex. 23 | 100.0 | 50% | 0.005 | 264 | 5 | 3 |
| Ex. 25 | 100.0 | 20% | 0.003 | 186 | 4 | — |
| Ex. 26 | 100.0 | 46% | 0.006 | 572 | 5 | 3 |
| Ex. 27 | 100.0 | 68% | 0.005 | 24 | 5 | 2 |
| Ex. 28 | 100.0 | 43% | 0.006 | 781 | 5 | 3 |

FIGS. 3 and 4 show SEM images of the coatings of Example 3 and Comparative Example 1. The SEM images were obtained as follows: a coating 30 minutes after formation was subjected to vapor deposition with gold, and was observed using an electron microscope (JEOL. JSM-6510) in a state of 5000 times magnification at an acceleration voltage of 10 kV, and an image thereof was captured. As shown in FIG. 3, the coating of Example 3 had binding portions at which fibers were bound to each other at fiber intersections.

The invention claimed is:

1. A coating formation method for forming a coating on a surface of a coating formation target, comprising
electrostatically spraying a composition directly onto the coating formation target, thereby forming a coating comprising a deposit comprising fibers,
wherein the composition consists of a component (a), a component (b), a component (c), and optionally a component (d) below:
(a) 60% by mass to 94% by mass of one or more volatile substances selected from the group consisting of water, ethanol, 1-butanol;

(b) 6% by mass to 40% by mass of a polymer having coating formability selected from the group consisting of a polyvinyl butyral resin, and (alkylacrylate/octylacrylamide)copolymer;

(c) 1.5% by mass to 20% by mass of a liquid agent which is in a liquid form at 20° C. selected from the group consisting of glycerin, polyglyceryl-2-diisostearate, polyglyceryl-10-diisostearate, diethylsebacate, dimethyl polysiloxane, squalene, liquid paraffin, neopentyl glycol dicaprate, jojoba oil, isononyl isononanoate, and dipropylene glycol; and (d) optionally, one or more components selected from the group consisting of a coloring pigment, an extender pigment, a dye, a surfactant with an HLB value of more than 10, a UV protection agent, an aromatic substance, a repellent, an antioxidant, a stabilizer, an antiseptic, an antiperspirant, and a vitamin, wherein the coating comprises a deposit comprising continuous fibers and the fibers are formed from the polymer having coating formability by the electrostatic spraying of the composition, wherein the mass ratio (c)/((b)+(c)) is from 0.05 to 0.75, wherein the content of said component (a) in said composition is 50% by mass or more, wherein the content of said component (b) in said composition is from 6% by mass to 40% by mass, and wherein said continuous fibers are formed from said polymer during said electrostatically spraying of said composition.

2. The coating formation method according to claim 1, wherein:
said component (b) is a polyvinyl butyral resin.

3. The coating formation method according to claim 1, wherein:
said component (a) comprises (a1) ethanol and (a2) water.

4. The coating formation method according to claim 1, wherein the coating has, on a surface side of the fibers forming the coating, a liquid agent holding coating in which the component (c) is present.

5. The coating formation method according to claim 1, wherein the coating formation target is a human skin surface.

6. The coating formation method according to claim 1, wherein the component (a) comprises a component (a1) and a component (a2),
the component (a1) is one or more components selected from the group consisting of ethanol and butyl alcohol, and
the component (a2) comprises water.

7. The coating formation method according to claim 1, wherein the component (a) comprises (a1) ethanol and (a2) water and the component (b) is a polyvinyl butyral resin.

8. The coating formation method according to claim 1, wherein the content of said component (b) in said composition is from 6% by mass to 20.4% by mass.

9. The coating formation method according to claim 1, wherein said polymer (b) is soluble in said volatile substances (a).

* * * * *